US009377467B2

(12) United States Patent
Neves et al.

(10) Patent No.: US 9,377,467 B2
(45) Date of Patent: *Jun. 28, 2016

(54) PROTEIN DETECTION

(71) Applicant: ACQUASCIENCE LIMITED, Uckfield (GB)

(72) Inventors: Andre T. R. M. A. Neves, Uckfield (GB); Brian Page, Uckfield (GB)

(73) Assignee: ACQUASCIENCE LIMITED, Uckfield, Sussex (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/718,828

(22) Filed: May 21, 2015

(65) Prior Publication Data
US 2015/0253337 A1 Sep. 10, 2015

Related U.S. Application Data

(63) Continuation of application No. 14/184,048, filed on Feb. 19, 2014, which is a continuation of application No. PCT/GB2012/051171, filed on May 24, 2012.

(30) Foreign Application Priority Data

Aug. 19, 2011 (GB) .................................. 1114341.9
Sep. 23, 2011 (GB) .................................. 1116421.7

(51) Int. Cl.
G01N 33/68 (2006.01)
G01N 21/78 (2006.01)
C07K 1/14 (2006.01)
G01N 33/58 (2006.01)

(52) U.S. Cl.
CPC ............ *G01N 33/6839* (2013.01); *C07K 1/145* (2013.01); *G01N 33/583* (2013.01); *G01N 21/78* (2013.01); *G01N 2400/18* (2013.01); *Y10T 436/107497* (2015.01)

(58) Field of Classification Search
CPC ....... G01N 21/77; G01N 21/78; G01N 33/68; G01N 33/6803; G01N 33/6839; G01N 2400/18; C07K 1/14; C07K 1/26; C07K 1/145; Y10T 436/107497; Y10T 436/143333
USPC ............... 436/8, 17, 86, 88, 93, 94, 131, 164, 436/166; 252/408.1; 204/450, 466
See application file for complete search history.

(56) References Cited

U.S. PATENT DOCUMENTS

| 3,063,812 | A | 11/1962 | Collins |
| 4,023,933 | A | 5/1977 | Bradford et al. |
| 4,239,495 | A | 12/1980 | Gindler et al. |
| 5,563,057 | A | 10/1996 | Gellman et al. |
| 5,593,895 | A | 1/1997 | Cahill et al. |
| 2006/0270051 | A1 | 11/2006 | Jenkins et al. |
| 2008/0234208 | A1 | 9/2008 | Sun et al. |
| 2009/0005384 | A1 | 1/2009 | Miura et al. |
| 2009/0197348 | A1 | 8/2009 | Mallia et al. |
| 2009/0298185 | A1 | 12/2009 | Jones et al. |

FOREIGN PATENT DOCUMENTS

| DE | 19631020 A1 | 5/1998 |
| EP | 0304052 A2 | 2/1989 |
| EP | 2016421 | 11/2007 |
| EP | 2088434 A1 | 8/2009 |
| GB | 814223 A | 6/1959 |
| GB | 2437545 A | 10/2007 |
| JP | 56069556 A | 6/1981 |
| JP | 56103366 A | 8/1981 |
| JP | 60178359 A | 9/1985 |
| JP | 61133138 A | 6/1986 |
| JP | 2009204808 A | 9/2009 |
| WO | WO0044928 A2 | 8/2000 |
| WO | WO2007125372 A1 | 11/2007 |
| WO | WO2009144419 A1 | 12/2009 |

OTHER PUBLICATIONS

Nov. 24, 2011 Search Report in United Kingdom Application No. GB1114341.9.
Jan. 17, 2012 Search Report in United Kingdom Application No. GB1114341.9.
Jan. 13, 2012 Search Report in United Kingdom Application No. GB1116421.7.
May 14, 2012 Search Report in United Kingdom Application No. GB1116421.7.
The International Search Report and Written Opinion dated Sep. 5, 2012 in International Application No. PCT/GB2012/051171.
Zhu, Xiashi et al. "Determination of Protein by hydroxypropyl-B-cyclodextrin sensitized fluorescence quenching method with erythrosine sodium as a fluorescence probe." College of Chemistry & Chemical Engineering, Yangzhou University, CN. Analytica Chimica Acta 596 (2007) pp. 298-302.
Yasumitsu, Hidetaro et al. "CGP stain: An inexpensive, odorless, rapid, sensitive, and in principle in vitro methylation-free Coomassie Brilliant Blue stain." Analytical Biochemistry 406 (2010) pp. 86-88.
Luo, Xi-Yuan et al. "Detergent Interference with Lowry Assay of Bovine Milk Fat Globule Membrane Protein." Biochemical Archives, vol. 13, 1997, pp. 319-326.
Tsa, Tsjimin et al. "Modification of Physical Characteristics of Microcrystalline Cellulose by Codrying with B-Cyclodextrins." Journal of Pharmaceutical Sciences 117, vol. 87, No. 1, Jan. 1998. pp. 117-122.
Iacovache, Ioan et al. "The 2DX robot: A membrane protein 2D crystallization Swiss Army knife." Journal of Structural Biology, 169 (2010) pp. 370-378.
Xu, Pei-Pei et al. "Interference by Cyclodextrins in Protein Determination by the Bradford Method." Microchemical Journal, 49 (1994) pp. 85-90.

*Primary Examiner* — Maureen Wallenhorst
(74) *Attorney, Agent, or Firm* — Dorsey & Whitney LLP

(57) ABSTRACT

The present invention relates to reagents for separating proteins from detergent, reagents for detecting proteins in the presence of a detergent, and methods of using the same. The separating reagents contain a cyclic oligomer such as cyclodextrin and a cellulose derivative such as 2-hydroxyethyl cellulose. When used in combination with standard protein-complexing dyes, the reagents allow detection of proteins in electrophoresis gels at nanogram levels.

18 Claims, 5 Drawing Sheets
(2 of 5 Drawing Sheet(s) Filed in Color)

PROTEIN DETECTION

The present invention relates to reagents for separating proteins from detergent, reagents for detecting proteins in the presence of a detergent, and methods of using the same.

BACKGROUND OF THE INVENTION

Proteins are commonly found in combination with detergents. For example, detergents are often used to disrupt cell membranes to break them apart when extracting proteins from cells. Detergents are also typically used when separating protein mixtures using gel electrophoresis. Because detergents adversely affect the colour change on binding of Coomassie dyes to protein, the detergent must be removed by several wash steps, resulting in extended and convoluted staining procedures. Some detergents such as sodium dodecyl sulphate are also known to denature proteins. Therefore, it is often desirable to separate the proteins from the detergents prior to their subsequent use.

WO2007/125372 discloses protein detection reagents that contain Coomassie dyes in combination with a dextrin such as cyclodextrin. Allegedly, the presence of the dextrin overcomes the difficulties with detergents being present in combination with the Coomassie dye. Consequently, there is no need to carry out the laborious washing steps that are typically needed. However, it has been found that the reagents disclosed in WO2007/125372 containing an acid such as phosphoric acid often suffer from poor stability and have high background staining due to unwanted precipitation.

There remains a need to provide further reagents for separating proteins from detergents. There also remains a need to provide further reagents for the detection of protein that have improved sensitivity and stability.

SUMMARY OF THE INVENTION

The present invention provides a composition (hereinafter the "separating composition") for separating a protein from a detergent, said composition comprising
  a) a cellulose derivative, and
  b) a cyclic oligomer.

The present invention also provides a method (hereinafter the "separating method") for separating protein from a detergent, said method comprising
  1) contacting a sample containing a protein and a detergent with a solution comprising
    a) a cellulose derivative, and
    b) a cyclic oligomer; and
  2) separating the protein from the detergent.

The present invention also provides a method (hereinafter the "staining method") for detecting and/or quantifying proteins comprising
  i) contacting a protein-containing sample with a first solution comprising a cyclic oligomer;
  ii) contacting the protein-containing sample with a second solution comprising a protein-complexing dye; and
  iii) detecting and/or quantifying the formation of a dye/protein complex.

Preferably, at least one of the first or second solutions comprises an acid having a pKa of 4 or less.

Preferably, the first solution comprises a cellulose derivative.

The present invention also provides a composition (hereinafter the "staining composition") for detection of proteins comprising:
  a) a protein-complexing dye;
  b) a cyclic oligomer; and
  c) a hydroxycarboxylic acid.

Preferably, the hydroxycarboxylic acid in the staining composition is tartaric acid.

Preferably, the staining composition comprises a cellulose derivative.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figures 1A, 1B:
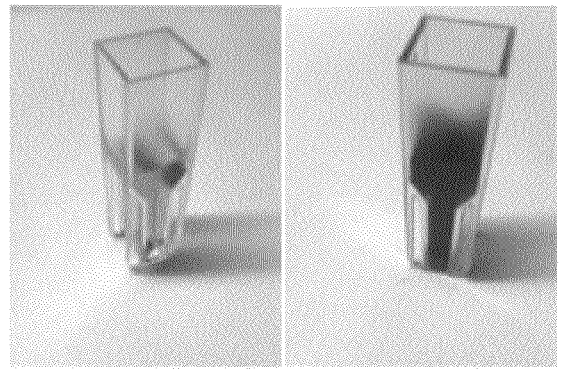
FIG. 1A shows a vial containing a formulation of the invention.
FIG. 1B shows a vial containing a standard dye.

The compositions of the present invention typically contain a cellulose derivative.

By "compositions of the present invention" is meant the "staining composition" and/or "separating composition" mentioned above. Likewise, by "methods of the present invention" is meant the "staining method" and/or "separating method" mentioned above.

By "cellulose derivative" is meant cellulose in which at least some of the free hydroxyl groups have been functionalised with alkyl, hydroxyalkyl or carboxyalkyl groups. Preferably, the cellulose derivative includes hydroxyalkyl or carboxyalkyl groups having two or three carbon atoms. Thus, preferred cellulose derivatives include hydroxyethyl, hydroxypropyl, carboxymethyl and carboxyethyl.

Preferred cellulose derivatives are selected from hydroxyethyl cellulose, hydroxypropyl cellulose, hydroxypropyl methyl cellulose, and carboxymethyl cellulose.

Preferably, the cellulose derivative is selected from hydroxyethyl cellulose, hydroxypropyl cellulose and hydroxypropyl methyl cellulose. Thus, preferred cellulose derivatives for use in the compositions of the present invention comprise repeat units having the following general formula:

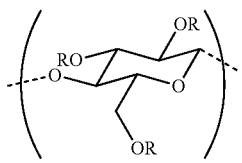

in which R denotes R', R" or R'", wherein
R' denotes H or CH$_2$CH$_2$OH (i.e. hydroxyethyl cellulose),
R" denotes H or CH$_2$CH(OH)CH$_3$ (i.e. hydroxypropyl cellulose), and
R'" denotes H, CH$_3$ or CH$_2$CH(OH)CH$_3$ (i.e. hydroxypropyl methyl cellulose).

Particularly preferred cellulose derivatives are selected from hydroxyethyl cellulose and hydroxypropyl methyl cellulose (i.e. R denotes R' or R"). The most preferred cellulose derivative is hydroxyethyl cellulose (i.e. R denotes R'), such as 2-hydroxyethyl cellulose.

The compositions of the invention also contain a cyclic oligomer.

By "cyclic oligomer" is meant an oligomer that is formed into a ring (or macrocycle). In other words, "cyclic oligomer" does not mean an oligomer of cyclic monomeric units (although these may be encompassed by the term, such as cyclic oligosaccharides), but rather an oligomer which is in the form of a continuous ring of monomeric units.

Suitable cyclic oligomers have hydrophilic groups such as hydroxyl to solubilize them in aqueous solutions. The cyclic oligomer is ring-shaped and has an inner cavity. Preferably, the cyclic oligomer is sized such that the inner cavity can accommodate a molecule, such as a dye, a surfactant or a detergent.

Preferable cyclic oligomers are selected from cyclic oligosaccharides, calixarene, cucurbituril, pillararene, or derivatives thereof.

By "cyclic oligosaccharide" is meant an oligosaccharide, or a compound made up of sugar molecules, which is formed into a ring (or macrocycle). Any type of cyclic oligosaccharide may in principle be used, although it is preferred to use cyclic oligosaccharides that contain only one type of sugar molecule.

Preferably, the cyclic oligosaccharide contains from 5 to 12 sugar molecules in the ring, more preferably from 6 to 8 sugar molecules, most preferably 6 sugar molecules.

Preferred cyclic oligosaccharides are selected from cyclodextrin (or cyclo-α(1→4)-glucoside), cyclodextran (cyclo-α (1→>6)-glucoside), cyclocurdlan (cyclo-β(1→3)-glucoside), cyclomannin (cyclo-α(1→4)-mannoside), cyclofructin (cyclo-β(1→2)-fructoside) and cyclogalactin (cyclo-β (1→4)-galactoside).

Particularly preferred cyclodextrins that can be used in the composition of the invention are selected from α-cyclodextrin (cyclo-α(1→4)-glucohexaoside), β-cyclodextrin (cyclo-α(1→4)-glucoheptaoside) and γ-cyclodextrin (cyclo-α (1→4)-glucooctaoside), with α-cyclodextrin (cyclo-α (1→4)-glucohexaoside) being the most preferred.

Preferred calixarenes are selected from calix[4]arene, calix [6]arene and calix[8]arene.

Preferred cucurbiturils are selected from cucurbit[6]uril and cucurbit[8]uril.

Preferred pillararenes are selected from pillar[5]arene and pillar[6]arene.

The term "cyclic oligomer" and "cyclic oligosaccharide" and each of the specific cyclic oligomers/oligosaccharides mentioned above also encompasses derivatives of these compounds, such as oligosaccharides in which the free hydroxyl groups have been functionalised, or cyclic oligomers that contain hydrophilic groups and/or groups that are capable of hydrogen bonding to water. These types of derivatives are preferred as they improve the solubility of the cyclic oligomer in water.

Suitable derivates include cyclic oligomers, for example any of the specific cyclic oligomers or cyclic oligosaccharides mentioned above, in which one or more of the free hydroxyl groups have been functionalised with C$_{1-4}$-alkyl, carboxymethyl, sulfonyl, acetyl, hydroxyethyl or hydroxypropyl. Derivative groups that are hydrophilic and/or capable of hydrogen bonding to water include carboxymethyl, sulfonyl, hydroxyethyl or hydroxypropyl.

The compositions of the present invention are typically aqueous solutions. As proteins can be sensitive to ionic strength, it is preferred to use deionised water to form the compositions of the invention, although this is not essential.

The separating composition typically leaves the protein free and available for further use, such as available to form a protein-dye complex. Therefore, the separating composition preferably does not contain any protein-complexing dye.

By "protein-complexing dye" is meant any moiety that shows a change in optical properties on formation of a protein-dye complex, such as a change in absorption spectra or a change in emission spectra.

Optional additional ingredients in the compositions of the present invention include a solubilising agents to help avoid aggregation of the proteins once the detergent-cyclic oligomer complex is formed. Suitable solubilising agents that may be used include alcohols such as methanol, ethanol and isopropanol, with ethanol being particularly preferred.

Typically amounts of each of the components in the separating composition of the present invention are summarized in the following table (all amounts are given as percentage w/v, i.e. grams per ml):

| Component | Typical amount | Preferred amount | Most preferred amount |
| --- | --- | --- | --- |
| Cyclic oligomer | 0.1-20% | 0.5-6% | 2-5% |
| Cellulose derivative | 0.01-2% | 0.05-1% | 0.1-0.5% |
| Solubiliser (e.g. ethanol) | 0-10% | 0.5-4% | 1-3% |

The amounts in the above table are independent of one another and representative of typical and preferred amounts of each of the components contained in the separating compositions of the present invention.

Other preferred ranges of cyclic oligomer include from 0.1 to 10% w/v, preferably 0.1 to 4% w/v, more preferably 0.5 to 4% w/v, e.g. 1 to 3% w/v.

Other preferred ranges of solubiliser include 0 to 5% w/v.

The separating composition finds use in separating proteins from detergents. It is therefore preferred that the separating composition itself does not contain any detergents/surfactants.

The separating composition can be made by simply mixing the ingredients together, for example to form an aqueous solution. However, it is preferred to ensure that each ingredient is fully dissolved prior to addition of the next. This may involve some moderate heating, for example to about 40-50° C. Typically, the cyclic oligomer is dissolved in deionised water mixed until an even solution is obtained (for example for about 30 minutes to 1 hour, perhaps longer if needed). The cellulose derivative can be added at this point, for example by forming a solution of cellulose derivative in deionised water and adding this to the solution containing the cyclic oligomer. Other orders of addition are of course possible, however.

Recently, it has been suggested that oligosaccharides such as cyclodextrin can be used to overcome difficulties associated with detergents and surfactants interfering with the colour changes of protein-staining dyes. Without wishing to be bound by theory, it is believed that the detergent forms a complex with the cyclic oligomer present in the separating composition of the invention. By using a suitable amount of one or more cyclic oligomers, the detergent can be trapped in an oligomer-detergent complex, thereby allowing its separation from the protein.

The separating composition of the invention is capable of trapping detergents/surfactants allowing them to be easily separated from the protein. The separating composition finds particular use when a protein/detergent mixture is contained in an electrophoresis gel. In such cases, the detergent is often present to mitigate protein agglomeration ensuring that the proteins are able to separate effectively in the gel. After separation, the gel can be exposed to a solution containing a cyclic oligomer to trap the detergent. The protein can then be separated from the detergent by continuing with the electrophoresis.

Thus, the present invention also provides a method (hereinafter the "separating method") for separating protein from a detergent, said method comprising 1) contacting a sample containing a protein and a detergent with a solution comprising
   a) a cellulose derivative, and
   b) a cyclic oligomer; and
2) separating the protein from the detergent.

In the separating method of the invention, the cyclic oligomer and detergent form a complex which is capable of being separated from the protein. The skilled person would be aware of suitable methods of separating a protein from the detergent. Suitable methods include, but are not limited to, centrifugation; chromatography such as size exclusion chromatography, ion exchange chromatography, affinity chromatography and high performance liquid chomatography (HPLC); and electrophoresis.

In a preferred embodiment, the sample containing a protein is an electrophoresis gel, and step 2) in the method comprises applying a potential to the gel to separate the protein.

While the separating composition of the invention is generally used to separate proteins and detergents, it finds particular use as a pre-treatment prior to staining with a protein-complexing dye. Thus, the separating compositions of the invention preferably form part of a kit comprising i) a first solution comprising
   a) a cellulose derivative, and,
   b) a cyclic oligomer; and
ii) a second solution comprising a protein-complexing dye.

Preferably, the first (or separating) solution does not contain a protein-complexing dye.

Protein-complexing dyes are well known in the art. Generally speaking, any Bradford assay reagents or other Coomassie protein staining reagents may be used in combination with the separating composition of the present invention. Examples of commercially available protein-complexing dyes that may be used include Coomassie Brilliant Blue G-250 and Coomassie Brilliant Blue R-250, available from Sigma-Aldrich.

For some protein staining dyes, such as Coomassie dyes in particular, a low pH is required in order to obtain the desired colour change when the dye complexes with a protein. Typically, the pH of the protein staining reagent needs to be below about 4, such as around pH 1-2. These low pH values are often achieved by adding an inorganic acid such as phosphoric acid.

However, it has been found that protein-staining reagents containing cyclic oligomers and a protein-complexing dye can have high levels of unwanted precipitate when using acids such as phosphoric acid. These precipitates result in high background noise which makes detection of small amounts of protein difficult if not impossible. Thus, typical detection levels for a "detergent tolerant" reagent containing a cyclodextrin, a Coomassie dye and phosphoric acid are around 20-30 ng (nanograms) of protein.

It has surprisingly been found that the separating composition of the invention reduces the amount of precipitates that form when an acid such as phosphoric acid is used in combination with a protein-complexing dye. As shown in the examples, phosphoric acid can be included in either the separating composition of the invention and/or in combination with the protein-complexing dye (i.e. in the first and/or second solutions in the kit of the invention) to provide a precipitate-free protein detection system.

The acid used in combination with the protein-staining dye has a pKa of 4 or less, preferably from 1 to 4, more preferably from 2 to 3.5. Suitable acids that may be included in the separating composition of the invention or used in combination with a protein-complexing dye include phosphoric acid, phosphorous (phosphonic) acid, periodic acid, selenic acid, maleic acid, oxalic acid, dichloroacetic acid, and hydroxycarboxylic acids (e.g. α-hydroxycarboxylic acids). Preferred acids are phosphoric acid and α-hydroxycarboxylic acids, e.g. tartaric acid.

Preferably, the separating compositions of the invention use an α-hydroxycarboxylic acid.

Preferred α-hydroxycarboxylic acids are selected from tartaric acid, malic acid, citric acid, isocitric acid, glycolic acid and lactic acid. Particularly preferred α-hydroxycarboxylic acids are selected from tartaric acid, malic acid, citric acid, and isocitric acid, with tartaric acid being the most preferred.

The use of an α-hydroxycarboxlic acid is preferred since they are generally less toxic than acids such as phosphoric acid. Moreover, α-hydroxycarboxylic acids such as tartaric acid are found to provide highly sensitive staining systems that are capable of detecting proteins at levels as low as 4 ng without issues arising from high background noise due to precipitates.

Typically, if present the amount of acid in the first and/or second solution in the kit of the invention is from 1 to 30% w/v (i.e. g/ml), preferably from 5 to 25% w/v, most preferably from 15 to 25% w/v. The skilled person would know that protein-complexing dyes may not function properly if the pH is too low. Consequently, the first and/or second solution would typically only contain from 5 to 15% w/v of a strong acid such as phosphoric acid, whereas a weaker acid such as tartaric acid may be present in higher amounts, such as 15 to 25% w/v.

It has surprisingly been found that the inclusion of a cellulose derivative such as 2-hydroxyethyl cellulose greatly improves the contrast of the staining of a protein gel which has been treated with either the separating or staining composition of the invention. The exact mechanism that leads to this effect is not fully understood. However, it is possible that the cellulose derivative stabilises the cyclic oligomer-detergent complex, further reducing the amount of free detergent and mitigating any interference that the detergent may have on the protein-dye complex.

The present invention also provides a method (hereinafter the "staining method") for detecting and/or quantifying proteins comprising i) contacting a protein-containing sample with a first solution comprising a cyclic oligomer;

ii) contacting the protein-containing sample with a second solution comprising a protein-complexing dye; and iii) detecting and/or quantifying the formation of a dye/protein complex.

Preferred staining methods of the invention use the preferred separating compositions of the invention as the first solution, and preferred kits of the invention with component i) in the kit corresponding to the first solution in the staining method and component ii) in the kit corresponding to the second solution in the staining method, said preferred compositions and kits being as set out above and in the claims.

In particular, the first solution in the staining method of the invention preferably contains a cellulose derivative, such as the cellulose derivatives set out above. It is also preferred that at least one of the first or second solutions comprises an acid having a pKa of 4 or less, such as the preferred acids set out above.

Preferably, the first and second solutions are aqueous solutions.

In step i) of the staining method of the invention, the cyclic oligomer forms a complex with any detergent that may be present in the protein-containing sample. Therefore, when the protein-complexing dye is added in step ii), the detergent is unable to interfere with protein-dye complex formation. The staining method therefore allows the detection of proteins at very low levels even if significant amounts of detergent are present in the initial protein-containing sample.

Consequently, the use of a cyclic oligomer such as a cyclodextrin in combination with a protein-staining dye provides a "detergent tolerant" protein staining system that does not require the laborious washing steps to remove any detergent that may be present. These reagents greatly simplify the protocols used to stain proteins during electrophoresis.

The second solution used in the staining method of the invention may be any type of protein-complexing dye, although Coomassie dyes are particularly preferred. Commercially available protein-complexing dyes may be used as the second solution in the staining method of the invention, either as supplied or suitably modified such as by adding an acid having a pKa of 4 or less.

The first (or separating) solution acts as a "pre-treatment" to remove (or negate the effect of) the detergent which is present. The second solution can then be used to stain the protein in accordance with the usual procedures for that dye. The advantage of using the pre-treatment (i.e. first solution) in accordance with the invention is self-evident, as any steps to remove the detergent which must usually be taken may be omitted.

The protein-containing sample may be in the form of a solution such as an aqueous solution (either dissolved or as a suspension), as a solid such as a precipitate, or in the form of a support containing the protein.

Typical supports that may contain a protein include a chromatography plate, filter paper, nitrocellulose membrane or resin, or a gel matrix, such as an electrophoresis gel. Suitable gel matrices are known to the skilled person, and include polyacrylamide gel and agarose gel.

When the protein-containing sample is a solution or suspension of the protein, it is typically not worthwhile separating the cyclic oligomer/detergent complex from the solution once formed. Instead, the protein-complexing dye can simply be added to the solution formed in step i) of the staining method.

When the protein-containing sample is in the form of a support containing the protein, the support may be removed from the first solution (e.g. by pouring off the first solution) after step i) prior to adding the second solution in step ii). This avoids the solution containing the protein-complexing dye becoming too dilute, which helps to keep the time needed to form the protein-dye complex to a minimum. Optionally, the support may be rinsed prior to step ii). However, this is not needed since the first and second solutions are compatible with one another.

Typically, the staining and separating methods of the invention are carried out at room temperature. However, slightly elevated temperatures, such as up to 50° C. may be used if needed.

The rate of cyclic oligomer/detergent complex formation will depend on the exact form of the protein-containing sample. For example, if the protein-containing sample is a solution, the rate of formation is near instantaneous. However, in the case that the protein is trapped within a matrix such as an electrophoresis gel, the step of contacting the protein-containing sample with the first solution typically takes up to 15 minutes in most cases, but may take up to 1 hour depending on the concentration of the detergent in the protein-containing sample. Similar timescales are needed for step ii) to form the protein-dye complex.

When being used to stain gels such as electrophoresis gels, the first solution is preferably heated in a microwave together with the gel for up to 30 seconds, e.g. 20 seconds. These values are for a typical 1000 W microwave. After microwaving, the composition and gel are typically left for eg. 15 minutes, either at room temperature (e.g. 20-25° C.) or at an elevated temperature such as 50° C. Elevated temperatures can be maintained by using a water bath, or any other suitable means. This protocol can optionally be repeated for step ii), if needed. However, the protocol for step ii) may vary slightly depending on the protein-complexing dye that is used. The skilled person would be aware of suitable protocols that should be used for any given protein-complexing dye.

Although these are preferred protocols, the examples show that the staining kit of the invention can be used at room temperature to stain electrophoresis gels in only 15 minutes. Typically, the method of the invention involves exposing the electrophoresis gel to the first solution for up to 30 minutes, e.g. from 5 to 15 minutes; pouring of the first solution; and exposing the electrophoresis gel to the second solution for up to 30 minutes, e.g. from 5 to 15 minutes. Of course, the longer the gel is exposed to the first and second solutions, the more sensitive the method will be, particularly if the gel is stained at elevated temperatures as set out above.

Thus, in preferred embodiments (especially when the protein-containing sample is an electrophoresis gel and high sensitivity is required), the staining method of the invention comprises, after the step of contacting the first solution with the protein-containing sample, heating the first solution and protein-containing sample (such as heating in a microwave for 10-30 seconds, preferably 15-20 seconds) and maintaining the solution and sample at a temperature of from 20-60° C., preferably from 20-50° C., for up to 1 hour, preferably for 5 to 30 minutes, more preferably from 5 to 20 minutes.

Advantageously, the use of a cyclic oligomer means that there is no need to remove detergents and/or surfactants prior to detecting the protein. Thus, electrophoresis gels can be stained using the composition of the invention without being washed after running the gel. In a preferred aspect, the present invention therefore relates to a method of detecting and/or quantifying a protein comprising a) providing a gel containing protein,
b) applying an electric field to the gel,
c) exposing the gel to a first solution comprising a cyclic oligomer,
d) optionally removing the gel from the first solution,
e) exposing the protein-containing sample to a second solution containing a protein-complexing dye, and
f) detecting and/or quantifying the dye/protein complex formation.

In such methods, it is preferred that the gel is not washed after step b) and prior to step c). Any suitable electrophoresis gel may be used in this method, such as a polyacrylamide or agarose gel.

By "optionally removing the gel from the first solution" in step d) is meant that the gel and the first solution are separated by any means, such that the first solution is no longer present when the gel is exposed to the second solution during step e). In practice, it may not be desirable to actually move the gel during step d), as electrophoresis gels are typically quite fragile. Instead, step d) typically comprises pouring off the first solution, such that the gel remains in the container which is being used in the method.

In the staining method of the invention, detecting the protein/dye complex may comprise quantifying the amount of protein/dye complex present so as to determine the amount or concentration of protein. Typically, the formation of the protein-dye complex results in a change in the spectroscopic properties of the dye, which can be detected and analysed using known methodology. For example, quantifying can be performed by methods which comprise measuring a change in absorption or emission spectra of the dye/protein complex. Quantifying may comprise for example measuring a colour change. For most protein-complexing dyes, absorbance is generally measured at a wavelength in the range of from about 400 to about 700 nm.

Using suitable real-time spectroscopic means allows the change in absorbance over time to be measured. For Coomassie brilliant blue G-250, absorbance is measured at a wavelength of about 595 nm, the absorbance maximum for this dye when complexed to protein. When using Coomassie brilliant blue G-250, protein can be detected by monitoring of the increase in absorbance at 595 nm due to formation of the dye/protein complex.

To determine protein concentration, the absorbance or emission measured can be compared with a standard value, standard set of values, or standard curve.

The methods of this invention are highly amenable to automation and analysis of large numbers of samples. Suitable high-throughput apparatus are commercially available, and would be known to the skilled person.

As mentioned above, the use of the separating composition of the invention avoids the issues that arise when using inorganic acids such as phosphoric acids in combination with a protein-complexing dye and a cyclic oligomer such as cyclodextrin. It has surprisingly been found that these disadvantages can also be overcome if a hydroxycarboxylic acid is used in an "all-in-one" staining composition.

The present invention therefore relates to a composition (referred to herein as a "staining composition") for detection of proteins comprising:
a) a protein-complexing dye;
b) a cyclic oligomer; and
c) a hydroxycarboxylic acid.

In some embodiments, the cyclic oligomer in the staining composition is not α-cyclodextrin (cyclo-α(1→4)-glucohexaoside).

Preferably, the hydroxycarboxylic acid in the staining composition is an α-hydroxycarboxylic acid such as tartaric acid, malic acid, citric acid, isocitric acid, glycolic acid or lactic acid. The most preferred hydroxycarboxylic acid is tartaric acid.

Preferably, the staining composition further comprises a cellulose derivative, such as any of the preferred cellulose derivatives mentioned above in the context of the separating composition. The most preferred cellulose derivatives are hydroxyethyl cellulose, hydroxypropyl cellulose, hydroxypropylmethyl cellulose and carboxymethylcellulose, with hydroxyethyl cellulose and particularly 2-hydroxyethyl cellulose being particularly preferred.

Typical amounts of the various components in the staining composition of the invention are shown in the following table table (all amounts are given as percentage w/v, i.e. grams per ml):

| Component | Typical amount | Preferred amount | Most preferred amount |
| --- | --- | --- | --- |
| Dye | 0.0001-0.1% | 0.0005-0.01% | 0.001-0.005% |
| Cyclic oligomer | 0.1-4% | 0.5-4% | 1-3% |
| Hydroxycarboxylic acid | 10-30% | 15-25% | 18-22% |
| Cellulose derivative | 0-2% | 0.05-1% | 0.1-0.5% |
| Solubiliser (e.g. ethanol) | 0-5% | 0.5-4% | 1-3% |

While the staining composition of the invention may be in the form of a solution, such as an aqueous solution, kits containing two or more solutions which are combined to form the staining composition of the invention also form part of the invention. Thus, the present invention also provides a kit comprising
a) a protein-complexing dye,
b) a cyclic oligomer, and
c) a hydroxycarboxylic acid,
wherein components a), b) and c) are present in two or more separate compositions that when combined form a composition for detection of proteins.

In preferred embodiments of the invention, the kit comprises
i) a composition comprising a protein-staining dye, and
ii) a composition comprising a cyclic oligomer and a hydroxycarboxylic acid,
wherein components i) and ii), when combined, form a composition for detection of proteins.

In such kits, the first solution preferably also comprises a hydroxycarboxylic acid, such as an α-hydroxycarboxylic acid. Preferred α-hydroxycarboxylic acids are mentioned above, with tartaric acid being the most preferred.

Providing the staining composition in the form of a kit is advantageous as it can increase the stability and shelf life of the composition as a whole.

Such kits also preferably contain a cellulose derivative in the second solution. Preferred cellulose derivatives are mentioned above, with 2-hydroxyethyl cellulose being the most preferred.

Such kits also preferably contain a solubiliser in the second solution. Preferred solubilisers are mentioned above, with ethanol being the most preferred.

Preferred types and amounts of cyclic oligomer, α-hydroxycarboxylic acid, optional cellulose derivative and optional solubiliser are mentioned above in relation to the separating compositions of the invention.

The staining composition of the invention may also be applied directly to a protein containing sample in an alternative method of the invention.

Thus, the invention also provides a method for detecting and/or quantifying protein comprising contacting a protein-containing sample with a solution comprising
 a) a protein-complexing dye,
 b) a cyclic oligomer, and
 c) a hydroxycarboxylic acid; and
 detecting and/or quantifying the dye/protein complex formation.

Preferably, the sample containing the protein is in the form of a support containing the protein, such as an electrophoresis gel.

Thus, particularly preferred methods using the staining composition comprise
 i) providing a gel containing protein,
 ii) applying an electric field to the gel,
 iii) exposing the gel to a staining composition of the invention, and
 iv) detecting and/or quantifying the dye/protein complex formation.

In such methods, the gel is preferably not washed after step ii) and prior to step iii). Any suitable electrophoresis gel may be used in this method, such as a polyacrylamide or agarose gel.

As noted above, the rate of dye/protein complex formation will depend on the exact form of the protein-containing sample. For example, in the case that the protein is trapped within a matrix such as an electrophoresis gel, the step of contacting the protein-containing sample with the staining composition of the invention typically takes up to 15 minutes in most cases, but may take up to 1 hour to effectively stain proteins that are only present at very low concentrations.

Typically, the staining composition is applied to an electrophoresis gel to stain the proteins using the same methodology as set out above for the separating composition. Thus, when being used to stain gels such as electrophoresis gels, staining composition of the invention is preferably heated in a microwave together with the gel for up to 30 seconds, e.g. 20 seconds. These values are for a typical 1000 W microwave. After microwaving, the composition and gel are typically left for eg. 15 minutes, either at room temperature (e.g. 20-25° C.) or at an elevated temperature such as 50° C. Elevated temperatures can be maintained by using a water bath, or any other suitable means.

As noted above, the use of the first (i.e. separating) and second solutions in the kit of the invention reduces the amount of precipitates that are formed when the protein-complexing dye is brought into contact with the sample containing the protein. Even so, best results are obtained when using an α-hydroxycarboxylic acid such as tartaric acid. Moreover, using cellulose derivatives improves the contrast of the dye/protein-complex particularly when present in an electrophoresis gel.

The present invention therefore also relates to the use of a hydroxycarboxylic acid, particularly an α-hydroxycarboxylic acid such as tartaric acid, to reduce the amount of precipitates in an acidified solution containing a protein-complexing dye.

The present invention also relates to the use of a cellulose derivative such as hydroxyethyl cellulose (e.g. 2-hydroxyethylcellulose) to enhance the staining of a dye/protein complex.

The invention also relates to the use of the combination of a cellulose derivative such as hydroxyethyl cellulose (e.g. 2-hydroxyethylcellulose) and a cyclic oligomer such as cyclodextrin (e.g. α-, β- or γ-cyclodextrin) to enhance the staining of a dye/protein complex.

Clearly, the precipitates in a composition for detecting proteins will inevitably provide an unclear background of any stained mixture, such as a stained electrophoresis gel.

The invention therefore relates to the use of the combination of a hydroxycarboxylic acid, particularly an α-hydroxycarboxylic acid such as tartaric acid, and a cellulose derivative such as hydroxyethyl cellulose (e.g. 2-hydroxyethylcellulose) to enhance the staining of a dye/protein complex.

The invention also relates to the use of the combination of a hydroxycarboxylic acid, particularly an α-hydroxycarboxylic acid such as tartaric acid, a cellulose derivative such as hydroxyethyl cellulose (e.g. 2-hydroxyethylcellulose) and a cyclic oligomer such as cyclodextrin (e.g. α-, β- or γ-cyclodextrin) to enhance the staining of a dye/protein complex.

By "enhance the staining" is meant making the dye/protein-complex easier to identify in the stained mixture, for example by improving the contrast in a gel containing a protein which has been exposed to a protein-complexing dye. This improvement may be by improving the dye/protein-complex formation or by reducing the amount of background in regions that do not contain any protein, or by both. The improvement in stain enhancement may be determined by calculating the signal to noise ratio, for example by using densitometry.

Thus, viewed from another aspect, the present invention relates to the use of a cellulose derivative such as hydroxyethyl cellulose (e.g. 2-hydroxyethylcellulose) to improve the signal/noise ratio of a stained dye/protein complex in a gel, preferably as determined by densitometry.

The invention also relates to the use of the combination of a cellulose derivative such as hydroxyethyl cellulose (e.g. 2-hydroxyethylcellulose) and a cyclic oligomer such as cyclodextrin (e.g. α-, β- or γ-cyclodextrin) to improve the signal/noise ratio of a stained dye/protein complex in a gel, preferably as determined by densitometry.

The invention also relates to the use of the combination of a hydroxycarboxylic acid, particularly an α-hydroxycarboxylic acid such as tartaric acid, and a cellulose derivative such as hydroxyethyl cellulose (e.g. 2-hydroxyethylcellulose) to improve the signal/noise ratio of a stained dye/protein complex in a gel, preferably as determined by densitometry.

The invention also relates to the use of the combination of a hydroxycarboxylic acid, particularly an α-hydroxycarboxylic acid such as tartaric acid, a cellulose derivative such as hydroxyethyl cellulose (e.g. 2-hydroxyethylcellulose) and a cyclic oligomer such as cyclodextrin (e.g. α-, β- or γ-cyclodextrin) to improve the signal/noise ratio of a stained dye/protein complex in a gel, preferably as determined by densitometry.

In the above uses, the cellulose derivative is preferably present as part of a solution (i.e. the cellulose derivative is not a solid matrix). The invention therefore preferably relates to the use of a solution of a cellulose derivative, optionally in combination with a hydroxycarboxylic acid and/or a cyclic oligomer, to achieve the above mentioned effects.

The improved signal/noise ratio is achievable even if the first solution is removed prior to adding the second solution in the method of the invention. This is believed to be due to the cellulose derivative impregnating or coating the gel during step i) of the method of the invention. Therefore, even if the first solution is removed and the gel rinsed prior to step ii), at least some of the cellulose derivative is retained in the gel to give rise to an improvement in the signal to noise ratio.

The same considerations apply to the α-hydroxycarboxylic acid, which may be present in the first and/or second solution. Thus, even if the α-hydroxycarboxylic acid is included only in the first solution, the acid impregnates the gel and is retained even if the first solution is removed. The acid can therefore give rise to an improvement in the signal/noise ratio even if it is not contained in the second solution. Of course, best results are obtained when using an α-hydroxycarboxylic acid in both the first and second solution.

The invention will be further described with reference to the following non-limiting Examples and Figures in which:

FIG. 1 shows vials with Formulation A (FIG. 1*a*) and Instant Blue (FIG. 1*b*)

Figure 2:
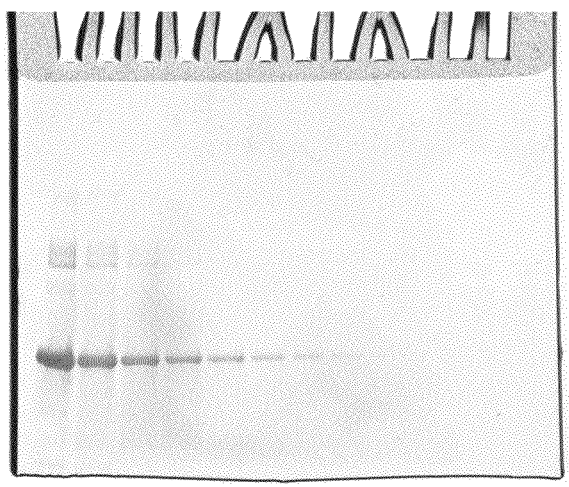
FIG. 2 shows a an unwashed gel stained with a formulation of the invention.

FIG. 2 shows an unwashed gel stained with Formulation A

Figure 3:
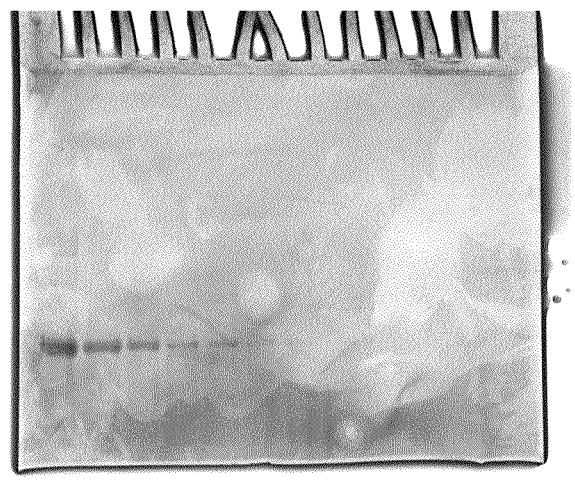
FIG. 3 shows an unwashed gel stained with a standard dye.

FIG. 3 shows an unwashed gel stained with Instant Blue

Figure 4:
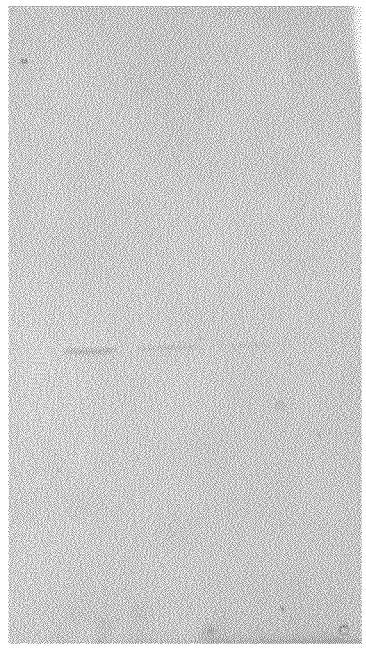
FIG. 4 shows a gel obtained using a composition of the invention.

FIG. 4 shows the gel obtained from Example 2a

Figure 5:
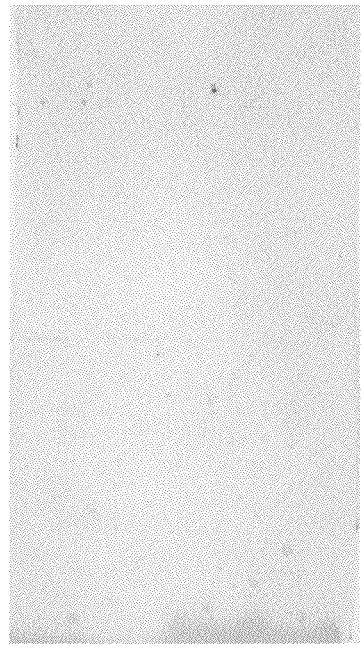
FIG. 5 shows another gel stained using a composition of the invention.

FIG. 5 shows the gel obtained from Example 2b

Figure 6:
FIG. 6 shows another gel stained using a composition of the invention.

FIG. 6 shows the gel obtained from Example 2c

Figure 7:
FIG. 7 shows another gel stained using a composition of the invention.

FIG. 7 shows the gel obtained from Example 3a

Figure 8:
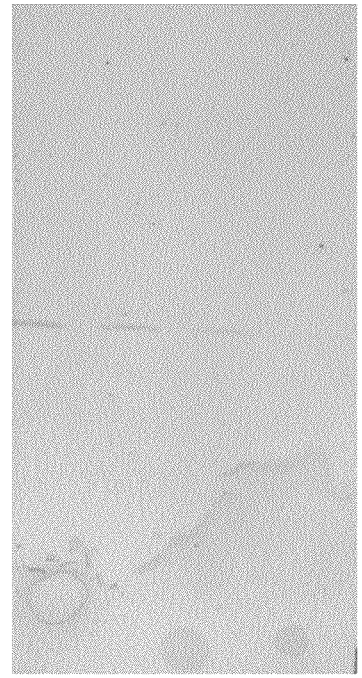
FIG. 8 shows another gel stained using a composition of the invention.

FIG. 8 shows the gel obtained from Example 3b

Figure 9:
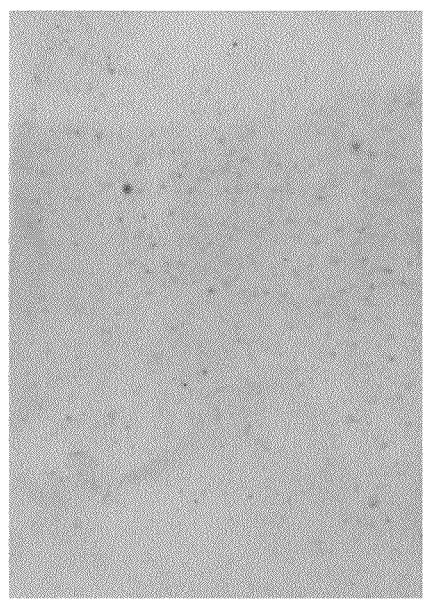
FIG. 9 shows another gel stained using a composition of the invention.

FIG. 9 shows the gel obtained from Example 3c

Figure 10:
FIG. 10 shows another gel stained using a composition of the invention.

FIG. 10 shows the gel obtained from Example 3d

Figures 11, 12:
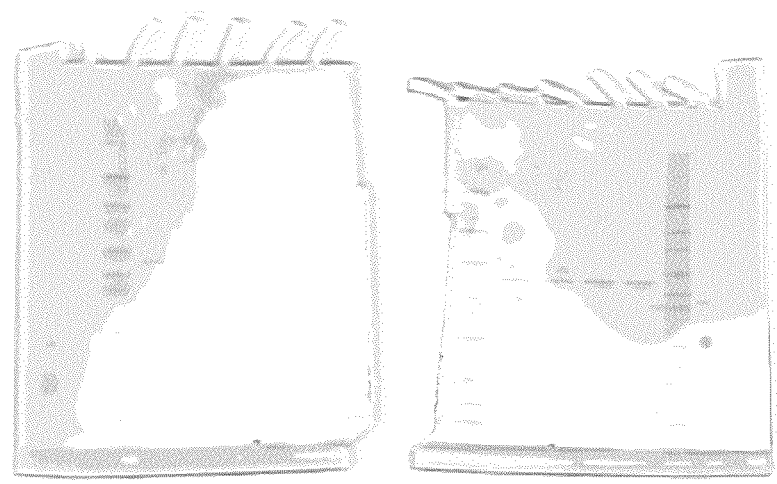
FIG. 11 shows a scanned image of a gel stained using a composition of the invention.
FIG. 12 shows a scanned image of a gel stained using another composition of the invention.

FIG. 11 shows the scans of gels stained with Formulation B

FIG. 12 shows the scans of gels stained with Formulation C

Figure 13:
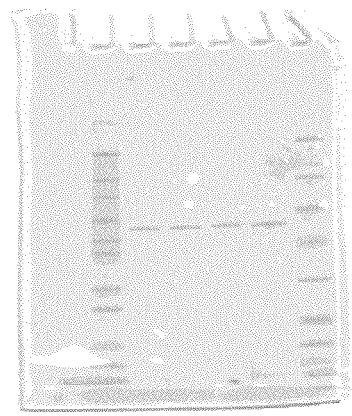
FIG. 13 shows a scanned image of a gel stained using another composition of the invention.

FIG. 13 shows the scans of gels stained with Formulation D

FIG. 14 shows the signal/noise ratio of gels stained with Formulation A and Instant Blue

EXAMPLE 1

The following formulation was prepared by mixing the ingredients in deionised water:

Formulation A:

| | |
|---|---|
| Tartaric acid | 20% w/v |
| α-Cyclodextrin | 2% w/v |
| Ethanol | 2% w/v |
| 2-Hydroxyethyl cellulose | 0.3 w/v |
| G250 dye | 0.0015% w/v |

As a comparison, "Instant Blue" was obtained from Expedeon Limited, which is believed to contain phosphoric acid, α-cyclodextrin, ethanol and a Coomassie dye, in line with the examples of WO2007/125372.

FIG. 1*a* shows a vial containing Formulation A, while FIG. 1*b* shows a vial containing Instant Blue. These Figures clearly show that the staining formulation of the invention was clear with no precipitates and had a light blue/green colour. In contrast, Instant Blue was turbid brown with significant amounts of suspended particles/precipitate.

These formulations were used to stain a PAGE gel containing various concentrations of BSA. The unwashed gels after staining for 1 hour are shown in FIGS. 2 and 3. The high levels of precipitates in Instant Blue make it difficult to see low levels of BSA against the background.

This example clearly shows the high level of precipitates in protein-staining solutions that contain a cyclic oligomer such as cyclodextrin together with phosphoric acid.

EXAMPLE 2

The following formulations were prepared by mixing the ingredients in deionised water:

| Formulation I-1 | |
|---|---|
| Tartaric acid | 20% w/v |
| α-Cyclodextrin | 4% w/v |
| Ethanol | 2% w/v |
| 2-Hydroxyethyl cellulose | 0.3 w/v |

| Formulation I-2 | |
|---|---|
| Phosphoric acid | 10% w/v |
| α-Cyclodextrin | 4% w/v |
| Ethanol | 2% w/v |
| 2-Hydroxyethyl cellulose | 0.3 w/v |

| Formulation I-3 | |
|---|---|
| α-Cyclodextrin | 4% w/v |
| Ethanol | 2% w/v |
| 2-Hydroxyethyl cellulose | 0.3 w/v |

| Formulation II-1 | |
|---|---|
| G250 dye | 0.013% w/v |
| Tartaric acid | 20% w/v |

| Formulation II-2 | |
|---|---|
| G250 dye | 0.013% w/v |
| Phosphoric acid | 10% w/v |

PAGE gels containing various concentrations of BSA were stained using the following combinations of formulations I and II shown above:

| Example | Pretreatment | Stain |
|---|---|---|
| 2a | I-1 | II-1 |
| 2b | I-2 | II-2 |
| 2c | I-3 | II-2 |

The PAGE gels were first exposed to pretreatment I for 10 minutes at room temperature. After exposure, the treatment solution was poured off, and the staining solution II was added. The gel was then left for a further 5 minutes at room temperature before the staining solution was removed.

The stained gels from 2a, 2b and 2c are shown in FIGS. 4, 5 and 6 respectively. These gels clearly show that the kit according to the invention can be used in combination with acids such as phosphoric acid without suffering from any issues of precipitation. Moreover, a comparison between FIGS. 4 and 5/6 shows that the stained bands are much clearer when using tartaric acid.

EXAMPLE 3

The following formulations were prepared by mixing the ingredients in deionised water:

| Formulation I-4 | |
| --- | --- |
| α-Cyclodextrin | 4% w/v |
| Ethanol | 2% w/v |
| 2-Hydroxyethyl cellulose | 0.3 w/v |

| Formulation I-5 | |
| --- | --- |
| Tartaric acid | 20% w/v |
| Ethanol | 2% w/v |
| 2-Hydroxyethyl cellulose | 0.3 w/v |

| Formulation I-6 | |
| --- | --- |
| Tartaric acid | 20% w/v |
| α-Cyclodextrin | 4% w/v |
| Ethanol | 2% w/v |

PAGE gels containing various concentrations of BSA were stained using the following combinations of formulations I and II shown above:

| Example | Pretreatment | Stain |
| --- | --- | --- |
| 3a | I-1 | II-1 |
| 3b | I-4 | II-1 |
| 3c | I-5 | II-1 |
| 3d | I-6 | II-1 |

The PAGE gels were first exposed to pretreatment I for 10 minutes at room temperature. After exposure, the treatment solution was poured off, and the staining solution II was added. The gel was left for a further 5 minutes at room temperature before the staining solution was removed.

The stained gels from examples 3a, 3b, 3c and 3d are shown in FIGS. 7, 8 9 and 10 respectively. The gels in FIGS. 7 and 8 show that tartaric acid need not be included in the first solution (i.e. the pretreatment). FIG. 9 clearly shows that no bands are visible if the cyclic oligomer is omitted from the pretreatment. Moreover, FIG. 10 shows that the bands are barely visible if the cellulose derivative is omitted from the pretreatment.

EXAMPLE 4

The following formulations were made by dissolving the various ingredients in deionised water:

Formulation B:

| | |
| --- | --- |
| Phosphoric acid | 20% w/v |
| α-Cyclodextrin | 2% w/v |
| Ethanol | 2% w/v |
| G250 dye | 0.0045% w/v |

Formulation C:

| | |
| --- | --- |
| Tartaric acid | 20% w/v |
| α-Cyclodextrin | 2% w/v |
| Ethanol | 2% w/v |
| G250 dye | 0.0045% w/v |

Formulation D:

| | |
| --- | --- |
| Tartaric acid | 20% w/v |
| α-Cyclodextrin | 2% w/v |
| Ethanol | 2% w/v |
| 2-Hydroxyethyl cellulose | 0.3 w/v |
| G250 dye | 0.0045% w/v |

PAGE (PolyAcrylamide Gel Electrophoresis) was completed under standard conditions, using commercial gel products. Samples of commercially available and purchased Bovine serum albumin (standards) were created and run on the gel(s). Commercial markers were also included. Once the electrophoresis had completed the gels were removed from their plastic sheath and inserted into a small trough containing one of the formulations above. Identical gels were run and tested using each formulation. Staining times were identical for each formulation FIGS. 11 to 13 shows scans of the stained gels.

The middle four bands in the gel are the test bands of interest, with the outer lanes being standard markers. The gel pictures were obtained on a scanner, which resulted in the gel background being either light grey where an aqueous layer had been trapped between the gel and the glass screen of the scanner, or white where an air layer (or bubble) was between the gel and the screen.

Even though there are differences in the background due to the presence or absence of the aqueous layer between the gel and the glass plate of the scanner, the results in FIGS. 11-13 clearly show that using tartaric acid in place of phosphoric acid improved the contrast in the four test bands, making them easier to identify (see FIGS. 11 and 12). Moreover, FIGS. 12 and 13 show that adding 2-hydroxyethyl cellulose results in even greater contrast between the stained protein sample and the background.

EXAMPLE 5

Figure 14A:
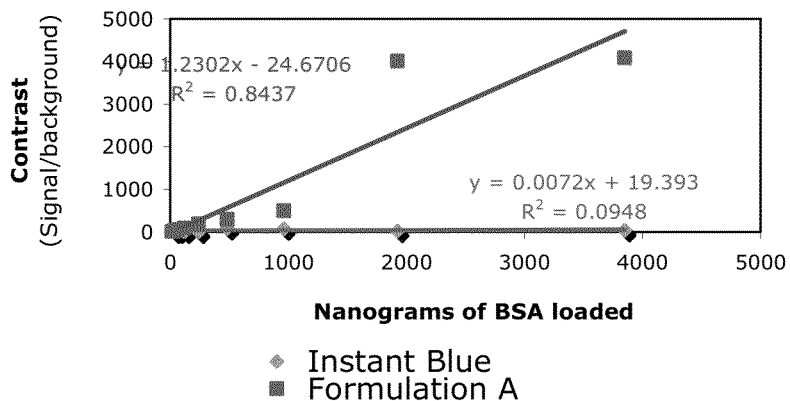
FIGS. 14A-14C show plots of the visible contrast of gels stained with compositions of the invention, compared to visible contrast of gels stained with standard dyes.
Figure 14B:
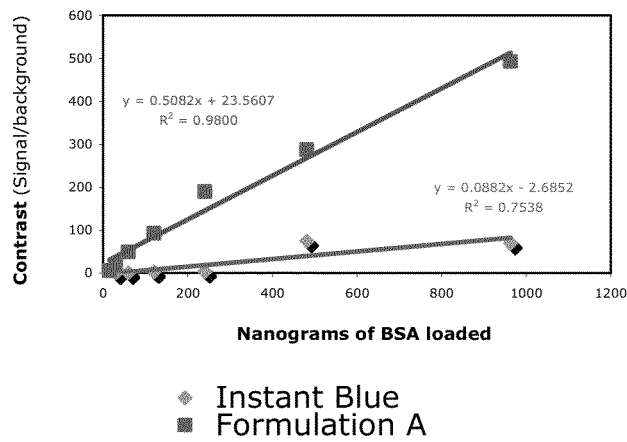

Formulation A and Instant Blue as described above was used to stain a PAGE gel containing various concentrations of BSA. The ratio of the stained protein to the background was measured via densitometry. The results are shown in FIGS. 14*a-c*.

Figure 14C:
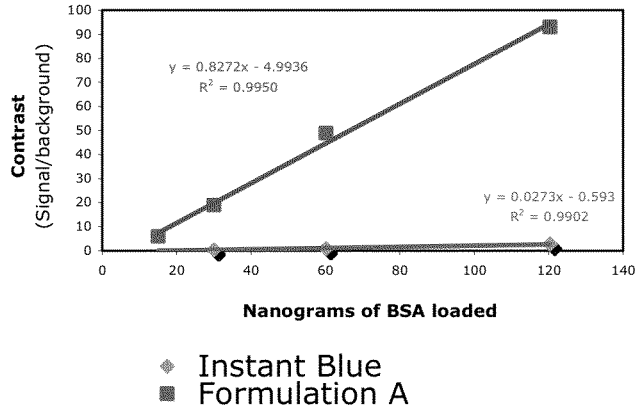

FIG. 14*c* clearly shows that Formulation A is able to detect proteins at concentrations below 20 ng. Moreover, each of FIGS. 14*a*, 14*b* and 14*c* demonstrate the significant improvements in signal to noise ratio obtained by using the staining composition according to the invention.

The invention claimed is:
1. A composition for detection of proteins comprising
   a) a protein-complexing dye,
   b) a cyclic oligomer, and
   c) tartaric acid.
2. The composition according to claim 1, further comprising a cellulose derivative.
3. The compositon of claim 2, wherein the cellulose derivative is 2-hydroxyethyl cellulose.

4. The composition according to claim 3, wherein the 2-hydroxyethyl cellulose is present in an amount of from 0.1 to 0.5-% w/v.

5. The composition according to claim 1, wherein the cyclic oligomer is cyclodextrin.

6. The composition of claim 5, wherein the cyclodextrin is a-cyclodextrin.

7. The composition of claim 5, wherein the cyclodextrin is present in an amount of from 0.1to 10% w/v.

8. The composition according to claim 5, wherein the cyclodextrin is present in an amount of from 1 to 3% w/v.

9. The composition according to claim 1, further comprising an alcohol.

10. The composition according to claim 9, wherein the alcohol is ethanol.

11. The composition according to claim 10, wherein the ethanol is present in an amount of from 1 to 3% w/v.

12. The composition of claim 1, wherein the protein-complexing dye is a Coomassie dye.

13. The composition of claim 1, wherein the composition is an aqueous solution.

14. A method of detecting and/or quantifying protein comprising contacting a protein- containing sample with a composition according to claim 1, and detecting and/or quantifying the formation of a dye/protein complex.

15. The method of claim 14, wherein the sample containing a protein is in the form of a support containing the protein.

16. The method of claim 15, wherein the support is an electrophoresis gel.

17. The method of claim 16, comprising the steps of
i) providing a gel containing protein,
ii) applying an electric field to the gel,
iii) exposing the gel to the composition; and
iv) detecting and/or quantifying the dye/protein complex formation.

18. The method of claim 17, wherein the gel is not washed after step ii) and prior to step iii).

* * * * *